(12) United States Patent
Fujihara (10) Patent No.: US 8,854,613 B2
(45) Date of Patent: Oct. 7, 2014

(54) SURFACE DEFECT INSPECTION APPARATUS AND SURFACE DEFECT INSPECTION METHOD

(75) Inventor: Katsumi Fujihara, Kawasaki (JP)

(73) Assignee: Fujitsu Limited, Kawasaki (JP)

(*) Notice: Subject to any disclaimer, the term of this patent is extended or adjusted under 35 U.S.C. 154(b) by 130 days.

(21) Appl. No.: 13/352,663

(22) Filed: Jan. 18, 2012

(65) Prior Publication Data

US 2012/0242984 A1 Sep. 27, 2012

(30) Foreign Application Priority Data

Mar. 22, 2011 (JP) ................................. 2011-063094

(51) Int. Cl.
*G01N 21/00* (2006.01)
*G01N 21/94* (2006.01)
*G01N 21/95* (2006.01)
*G01N 21/88* (2006.01)

(52) U.S. Cl.
CPC ........ G01N 21/94 (2013.01); *G01N 2021/8825* (2013.01); G01N 21/9501 (2013.01)
USPC .................... 356/237.4; 356/237.2; 356/237.6

(58) Field of Classification Search
USPC ............................................. 356/237.1–237.6
See application file for complete search history.

(56) References Cited

U.S. PATENT DOCUMENTS 5,835,220 A * 11/1998 Kazama et al. ............... 356/369
6,621,570 B1 * 9/2003 Danko ....................... 356/237.4
7,433,031 B2 * 10/2008 Xu et al. .................... 356/237.2
8,558,999 B2 * 10/2013 Kawaki et al. .............. 356/237.2
2005/0018182 A1 * 1/2005 Hyun et al. ................. 356/237.4
2007/0188744 A1 * 8/2007 Leslie et al. ................ 356/237.2

FOREIGN PATENT DOCUMENTS

| JP | 09-033446 | 2/1997 |
| JP | 2005-274256 | 10/2005 |
| JP | 2008-3103 | 1/2008 |
| JP | 2009-042076 | 2/2009 |
| JP | 2009-229105 | 10/2009 |

OTHER PUBLICATIONS

Office Action issued by the Japanese Patent Office on Jun. 24, 2014 in corresponding Japanese patent application No. 2011-063094.

* cited by examiner

*Primary Examiner* — Tarifur Chowdhury
*Assistant Examiner* — Isiaka Akanbi
(74) *Attorney, Agent, or Firm* — Staas & Halsey LLP (57) ABSTRACT

A surface defect inspection apparatus includes a light source that emits light to a first position on a surface of a target at an angle inclined with respect to the surface of the target, a first photodetector that detects first reflected light of the light from the light source, the first reflected light being reflected at the first position, a second photodetector that detects second reflected light of the light from the light source, the second reflected light being reflected at a second position, the second position being closer to the light source than the first position and being separated from the surface of the target by a given distance, and a determining unit that determines whether or not foreign matter is present on the surface of the target on a basis of detection results obtained from the first photodetector and the second photodetector.

10 Claims, 7 Drawing Sheets

| RANGE | PATTERN IN ILLUMINATION POSITION P2 | DEFECTIVE FOREIGN MATTER AT DESIGNATED HEIGHT P1 | SIGNAL LEVEL OF CAPTURED IMAGE SIGNAL A | SIGNAL LEVEL OF CAPTURED IMAGE SIGNAL B | SIGNAL LEVEL OF DIFFERENTIAL SIGNAL C | SIGNAL LEVEL OF BINARIZATION SIGNAL D |
|---|---|---|---|---|---|---|
| (1) | NO | NO | SUBSTANTIALLY 0 | MEDIUM TO HIGH | −MEDIUM TO −HIGH | LOW |
| (2) | NO | YES | HIGH | SUBSTANTIALLY 0 | +HIGH | HIGH |
| (3) | YES | NO | LOW TO MEDIUM | MEDIUM TO HIGH | SUBSTANTIALLY 0 TO −MEDIUM | LOW |
| (4) | YES | YES | HIGH | SUBSTANTIALLY 0 | +HIGH | HIGH |

SURFACE DEFECT INSPECTION APPARATUS AND SURFACE DEFECT INSPECTION METHOD

CROSS-REFERENCE TO RELATED APPLICATIONS

This application is based upon and claims the benefit of priority of the prior Japanese Patent Application No. 2011-063094, filed on Mar. 22, 2011, the entire contents of which are incorporated herein by reference.

FIELD

The embodiment discussed herein is related to a surface detect inspection apparatus and a surface defect inspection method.

BACKGROUND

A conventional known surface defect inspection apparatus includes a light projector that illuminates the surface of a target under inspection with light, a first light receiving unit that detects the amount light regularly reflected on the surface of the target, and a second light receiving unit that detects the amount of light irregularly reflected on the surface of the target. Japanese Laid-open Patent Publication No. 9-33446 is an example of related art.

If defective foreign matter with a predetermined height or more is present on a surface under inspection, when an inspection apparatus moves on the surface under inspection, the inspection apparatus may collide with the foreign matter and may be thereby damaged. Accordingly, it is desirable to check whether defective foreign matter with a predetermined height or more is present on the surface under inspection before the inspection apparatus is moved.

As with the above surface defect inspection apparatus, however, even if the amounts of light regularly and irregularly reflected on the surface under inspection can be measured, it may not be possible to check whether defective foreign matter with a predetermined height or more is present on the surface under inspection. In a case as well in which minute irregularities that may irregularly reflect light have been formed at a position, on the surface under inspection, onto which light is directed, a decision result may be affected by the irregularities.

SUMMARY

According to an aspect of the invention, a surface defect inspection apparatus includes a light source that emits light to a first position on a surface of a target at an angle inclined with respect to the surface of the target, a first photodetector that detects first reflected light of the light from the light source, the first reflected light being reflected at the first position, a second photodetector that detects second reflected light of the light from the light source, the second reflected light being reflected at a second position, the second position being closer to the light source than the first position and being separated from the surface of the target by a given distance, and a determining unit that determines whether or not foreign matter is present on the surface of the target on a basis of detection results obtained from the first photodetector and the second photodetector.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

DESCRIPTION OF EMBODIMENT

A surface defect inspection apparatus in an embodiment disclosed in this application will be described below in detail with reference to the drawings.

Figure 1:
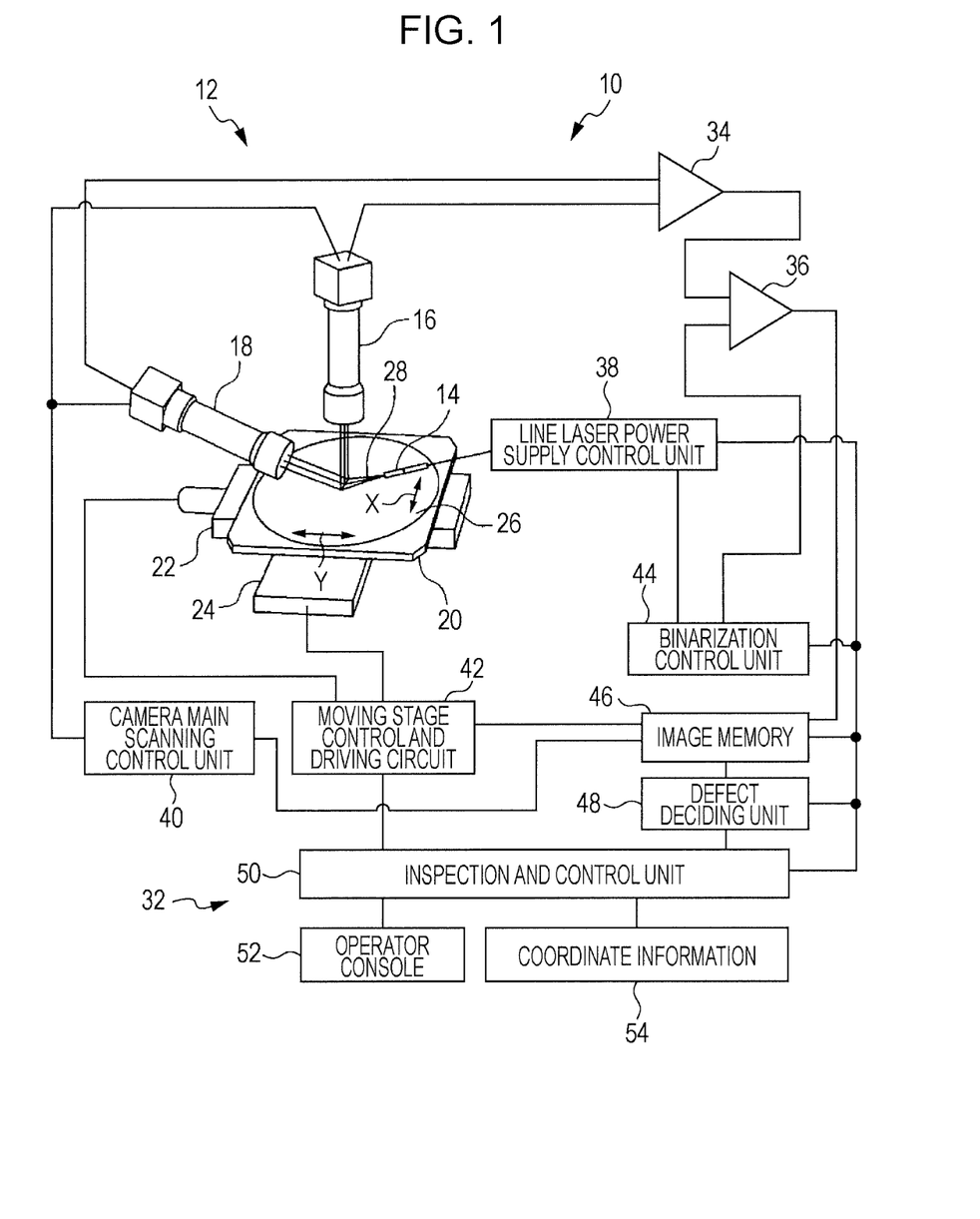
FIG. 1 illustrates the entire structure of a surface defect inspection apparatus in an embodiment.

As illustrated in FIG. 1, the surface defect inspection apparatus 10 in this embodiment has an inspection unit 12. The inspection unit 12 includes a line laser 14, a first line camera 16, a second line camera 18, a mounting table 20, a first moving stage 22, and a second moving stage 24. The line laser 14 is an example of a light source and a line light source. The first line camera 16 is an example of a first photodetector, and the second line camera 18 is an example of a second photodetector. The first moving stage 22 and second moving stage 24 are example of relatively moving units.

Figure 2:
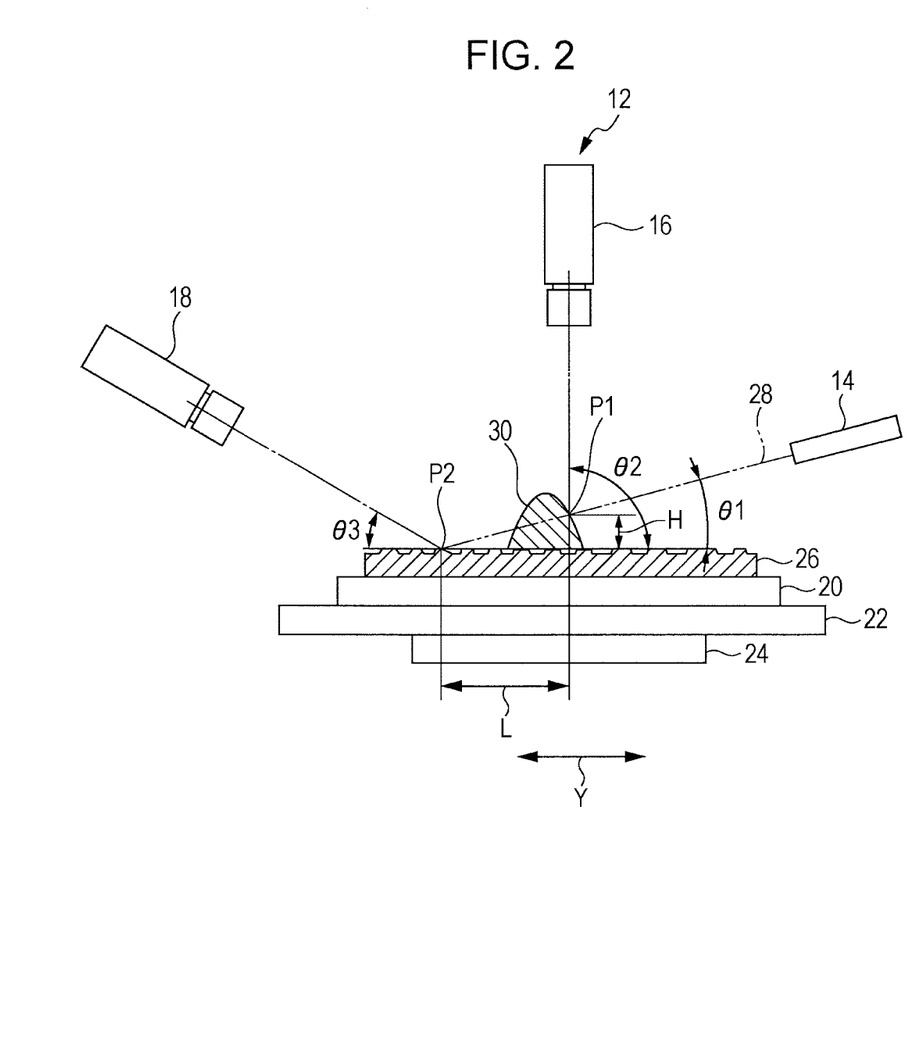
FIG. 2 illustrates the structure of an inspection unit included in the surface defect inspection apparatus in FIG. 1.

The line laser 14 is disposed so that an angle $\theta 1$ between a surface of a wafer 26, which is an example of a target under inspection mounted on the mounting table 20, and an optical axis becomes an acute angle, as illustrated in FIG. 2. The line laser 14 emits a line laser beam 28, which is an example of light and line light, toward the surface of the wafer 26 in an angled direction. The width direction of the line laser beam 28 is the X direction taken along the surface of the wafer 26, as illustrated in FIG. 1.

The first line camera 16 and second line camera 18 are placed so that their main scanning directions match the X direction. The main scanning range of the first line camera 16 and the main scanning range of the second line camera 18 overlap in the X direction. The first line camera 16 detects reflected light of the line laser beam 28 that has reflected at a position P1, illustrated in FIG. 2, at a predetermined height. The optical axis of the line laser beam 28 and the optical axis of the line laser 14 mutually intersect at the position P1 at the predetermined height.

The position P1 at the predetermined height is closer to the line laser 14 than an illumination position P2, on the wafer 26, onto which the line laser beam 28 is directed, and is separated from the surface of the wafer 26 by the predetermined height. The height H of the position P1 is set to a desired value as the predetermined height according to the height of defective foreign matter 30 to be detected. Specifically, assuming that a direction parallel to the surface of the wafer 26 and orthogonal to the X direction in FIG. 1 to be the Y direction, the height H of the position P1 at the predetermined height can be changed by changing a distance L in the Y direction between the position P1 at the predetermined height and the illumination position P2 or changing the angle θ1 described above. An angle θ2 between the optical axis of the first line camera 16 and the surface of the wafer 26 has been set to a right angle as an example.

The second line camera 18 detects reflected light of the line laser beam 28 that has reflected at the illumination position P2. The optical axis of the line laser beam 28 and the optical axis of the line laser 14 mutually intersect at the illumination position P2. The second line camera 18 is placed on the side opposite to the line laser 14, relative to the first line camera 16. An angle θ3 between the optical axis of the second line camera 18 and the surface of the wafer 26 has been set to an acute angle as an example.

The first moving stage 22, which is formed integrally with the mounting table 20, moves in the Y direction described above. The second moving stage 24 moves in the X direction in FIG. 1. The first moving stage 22 and second moving stage 24 have an actuator (not illustrated), by which the first moving stage 22 and second moving stage 24 are moved. When the first moving stage 22 and second moving stage 24 are moved, a measuring system including the line laser 14, first line camera 16, and second line camera 18 is relatively moved relative to the wafer 26.

The surface defect inspection apparatus 10 also has an operation unit 32 as illustrated in FIG. 1. The operation unit 32 includes an operation circuit 34, a binarization circuit 36, a line laser power supply control unit 38, a camera main scanning control unit 40, a moving stage control and driving circuit 42, a binarization control unit 44, an image memory 46, and a defect deciding unit 48. These components are implemented by electronic circuits or the like.

The operation unit 32 includes an inspection and control unit 50 and an operator console 52. The inspection and control unit 50 may be a personal computer, for example. The operations and functions of these components of the operation unit 32 will be described together with a wafer inspection method.

Next, the wafer inspection method in this embodiment will be described.

The wafer inspection method begins with inspection in which the surface defect inspection apparatus 10 described above is used to see whether defective foreign matter with a predetermined height or more is present on the surface of the wafer 26. Then, the wafer 26 undergoes electric inspection carried out by using a wafer inspection apparatus 60 illustrated in FIG. 7. First, the inspection carried out by using the surface defect inspection apparatus 10 will be described.

In the inspection carried out by using the surface defect inspection apparatus 10, the operator first inputs the size of the wafer 26, the height H of the position P1 at the predetermined height, the inspection range of the wafer 26, and other information on the operator console 52. The operator then sets the wafer 26 on the mounting table 20, after which the operator inputs a command to start the inspection on the operator console 52.

Figure 3:
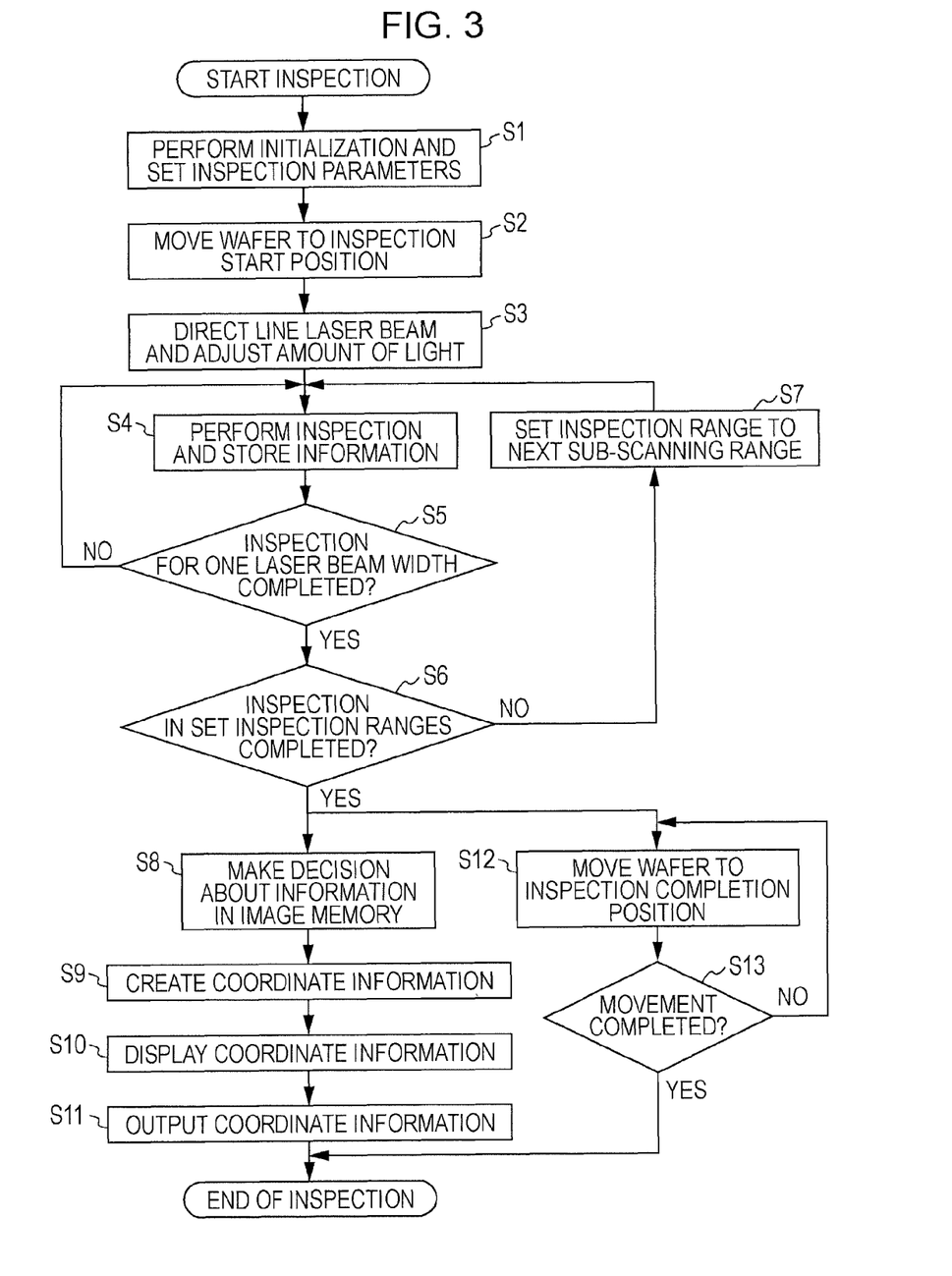
FIG. 3 is a flowchart illustrating the flow of processes executed by an inspection and control unit included in the surface defect inspection apparatus in FIG. 1.

When the operator console 52 receives the command to start the inspection, the inspection and control unit 50 executes the processes illustrated in FIG. 3.

Specifically, the inspection and control unit 50 first outputs an initialization command to the image memory 46 in step S1 so that the previous inspection results and other information stored in the image memory 46 are initialized. In step S1, the inspection and control unit 50 also sets inspection parameters according to the information input on the operator console 52. The inspection parameters include, for example, positions on the first moving stage 22 and second moving stage 24 at which to start inspection, the amount of movement, movement directions, the number of repetitive movements, and moving speeds. The inspection parameters also include the cycles of main scannings carried out by the first line camera 16 and second line camera 18, the signal level of the binarization reference signal, and other information used in inspection described below.

The inspection and control unit 50 then outputs a move-to-inspection-start-position command to the moving stage control and driving circuit 42 in step S2. Since the actuators (not illustrated) thereby operate, the first moving stage 22 and second moving stage 24 move and the wafer 26 moves to a predefined inspection start position.

The inspection and control unit 50 also outputs a driving command to the line laser power supply control unit 38 in step S3. The line laser 14 thereby emits the line laser beam 28, and the line laser beam 28 is directed onto the surface of the wafer 26 in an angled direction. At that time, the line laser power supply control unit 38 adjusts the amount of line laser beam 28 according to the driving command output from the inspection and control unit 50.

The inspection and control unit 50 then outputs an inspection start command to the moving stage control and driving circuit 42 in step S4. Since the relevant actuator (not illustrated) thereby operates, the first moving stage 22 is moved in the Y direction. When the first moving stage 22 is moved in the Y direction, move-to position information according to a position to which the first moving stage 22 is moved in the Y direction is output from the moving stage control and driving circuit 42 to the image memory 46. In this case, the moving stage control and driving circuit 42 is an example of a relative move-to position information output unit, and the move-to position information output from the moving stage control and driving circuit 42 is an example of relative move-to position information.

The inspection and control unit 50 also outputs a main scanning command to the camera main scanning control unit 40 in step S4. The first line camera 16 and second line camera 18 are thereby scanned by the camera main scanning control unit 40 in synchronization with each other. Captured image signals (serial signals) are then output from the first line camera 16 and second line camera 18 to the operation circuit 34 in sequence. The signal levels of these captured image signals are increased as the amounts of light detected by the first line camera 16 and second line camera 18 increases. The captured image signal from the first line camera 16 is input to a non-inverting input terminal of the operation circuit 34, and the captured image signal from the second line camera 18 is input to an inverting input terminal of the operation circuit 34. In the operation circuit 34, the captured image signal output from the second line camera 18 is subtracted from the captured image signal output from the first line camera 16.

The inspection and control unit 50 also outputs a signal output command to the binarization control unit 44 in step S4. At that time, the line laser power supply control unit 38 outputs, to the binarization control unit 44, a light amount signal appropriate for the amount of line laser beam 28. When the binarization control unit 44 receives this signal output command, the binarization reference signal having a signal level corresponding to the amount of light described above is output from the binarization control unit 44.

A differential signal output from the operation circuit 34 is input to a non-inverting terminal of the binarization circuit 36, and the binarization reference signal output from the binarization control unit 44 is input to an inverting terminal of the binarization circuit 36. In the binarization circuit 36, the differential signal output from the operation circuit 34 is compared with the binarization reference signal output from the binarization control unit 44, by which the differential signal is binarized and output from the binarization circuit 36 as a binarized signal.

Figure 4:
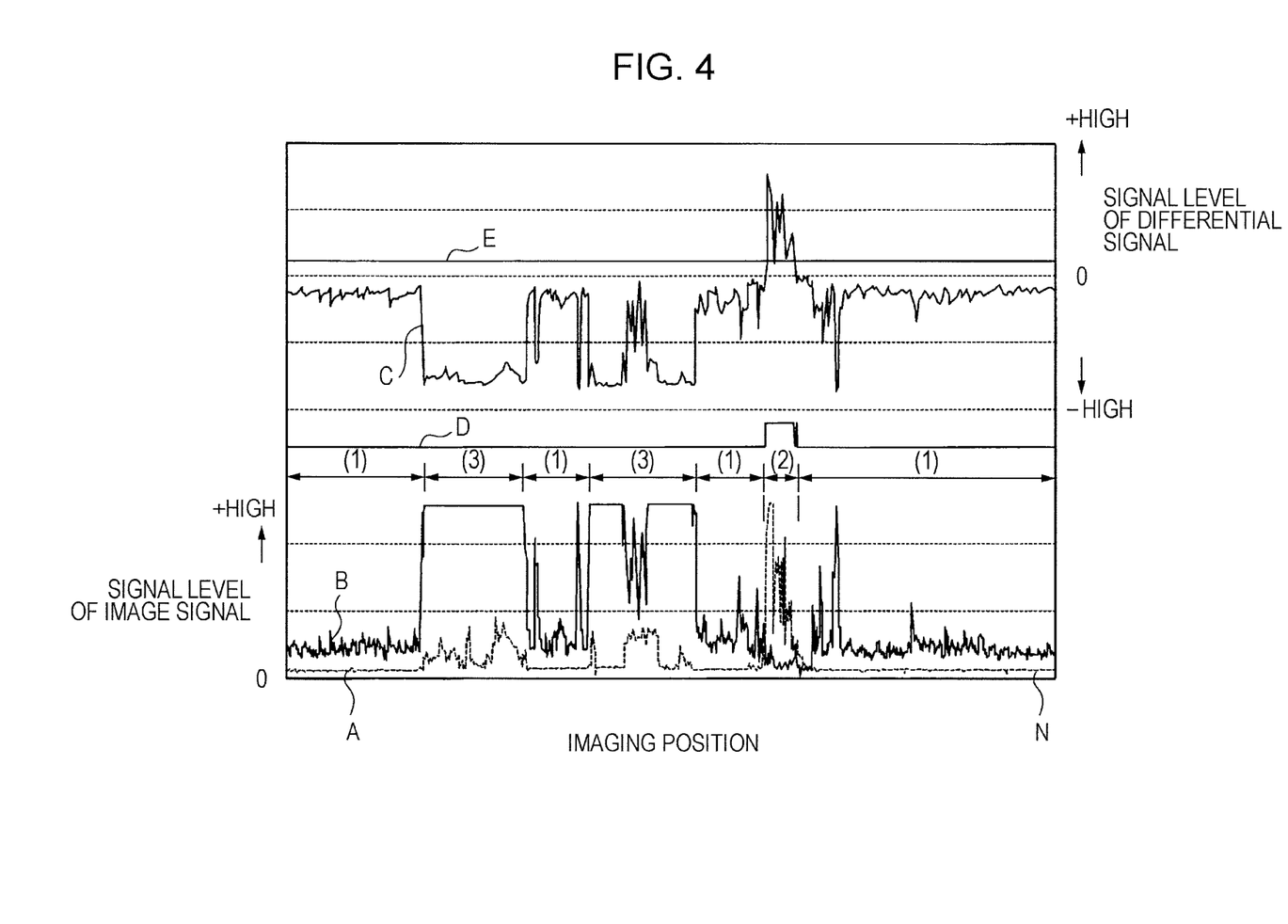
FIG. 4 illustrates waveforms of captured image signals, a differential signal, a binarized signal, and a binarization reference signal obtained by the surface defect inspection apparatus in FIG. 1.

FIG. 4 illustrates examples of the captured image signals output from the first line camera 16 and second line camera 18, the differential signal output from the operation circuit 34, the binarized signal output from the binarization circuit 36, and the binarization reference signal output from the binarization control unit 44.

In FIG. 4, the reference symbol A indicates the captured image signal output from the first line camera 16, the reference symbol B indicates the captured image signal output from the second line camera 18, the reference symbol C indicates the differential signal output from the operation circuit 34, and the reference symbol D indicates the binarized signal output from the binarization circuit 36. Furthermore, the reference symbol E indicates a binarized signal input to the binarization circuit 36. The horizontal axis indicates imaging positions, that is, the positions of a plurality of pixels included in the first line camera 16 and second line camera 18. A first vertical axis indicates the signal levels of the captured image signals A and B, and a second vertical axis indicates the signal level of the differential signal C.

Range (1) in FIG. 4 indicates, for example, a case in which the defective foreign matter 30 with the predetermined height or more is not present at the position P1 at the predetermined height illustrated in FIG. 2 and no convex pattern has been formed at the illumination position P2. In this case, since the defective foreign matter 30 is not present, the line laser beam 28 reaches the illumination position P2 and is reflected at the illumination position P2. The reflected light is detected by the second line camera 18. Accordingly, the signal level of the captured image signal B output from the second line camera 18 is increased in range (1). The reflected light at the illumination position P2 is not detected by the first line camera 16, so the signal level of the captured image signal A output from the first line camera 16 is substantially 0 in range (1). In range (1), the differential signal C has a lower signal level than the binarization reference signal E, so the binarized signal D is at a low level.

Range (2) in FIG. 4 indicates a case in which the defective foreign matter 30 with the predetermined height or more is present at the position P1 at the predetermined height as illustrated in, for example, FIG. 2, but no convex pattern has been formed at the illumination position P2. In this case, since the line laser beam 28 is reflected at the defective foreign matter 30 present at the position P1 at the predetermined height, the reflected light is detected by the first line camera 16. Accordingly, the captured image signal A output from the first line camera 16 is at a high level in range (2). The line laser beam 28 is shielded by the defective foreign matter 30, so the line laser beam 28 is not detected by the second line camera 18 regardless of whether a convex pattern has been formed at the illumination position P2. Accordingly, the signal level of the captured image signal B output from the second line camera 18 is substantially 0 in range (2). In range (2), the differential signal C has a higher signal level than the binarization reference signal E (the signal level of the differential signal C is positively high), and the binarized signal D is thereby at a high signal level.

Range (3) in FIG. 4 indicates, for example, a case in which the defective foreign matter 30 with the predetermined height or more is not present at the position P1 at the predetermined height illustrated in, for example, FIG. 2, but a convex pattern has been formed at the illumination position P2 on the surface of the wafer 26. In this case as well, since the defective foreign matter 30 is not present at the position P1 at the predetermined height, the line laser beam 28 reaches the illumination position P2. However, minute irregularities are present at the illumination position P2 due to the convex pattern, so the line laser beam 28 is irregularly reflected on these irregularities and the irregularly reflected light is detected by the first line camera 16 as stray light. The signal level of the captured image signal A output from the first line camera 16 is thereby increased in range (3). The reflected light of the line laser beam 28 at the illumination position P2 is also detected by the second line camera 18. Accordingly, the signal level of the captured image signal B output from the second line camera 18 is increased in range (3). Since the differential signal C has a lower signal level than the binarization reference signal E in range (3), however, the binarized signal D is at a low signal level as in the case in range (1) described above.

Figure 5:
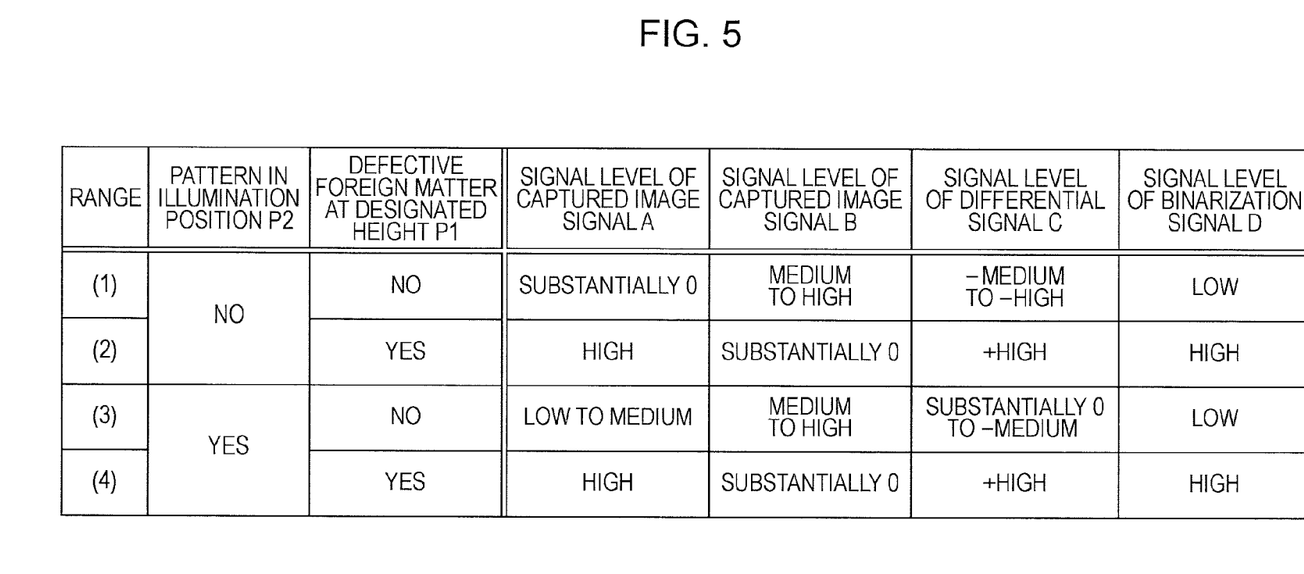
FIG. 5 illustrates relationships among the signal levels of the captured image signals, differential signal, and binarized signal in FIG. 4, presence of a pattern (irregularities) at an illumination position, and presence of defective foreign matter.

FIG. 5 illustrates relationships among ranges (1) to (4), presence of a convex pattern at the illumination position P2, and presence of defective foreign matter 30 at the position P1 at the predetermined height, the signal levels of the captured image signals A and B, the differential signal C, and the binarized signal D.

Range (4), which is not illustrated in FIG. 4, indicates, for example, a case in which the defective foreign matter 30 with the predetermined height or more is present at the position P1 at the predetermined height illustrated in FIG. 2 and a convex pattern at the illumination position P2 has been formed on the surface of the wafer 26.

The signal level of the captured image signal B depends on the degrees of the angle θ3 illustrated in FIG. 2. That is, when the angle θ3 is small, the signal level becomes high regardless of whether there is a pattern. When the angle θ3 is large, the signal level becomes intermediate when there is no pattern and becomes high when there is a pattern.

In FIG. 5, the captured image signals A and B can be taken an example of indicating a situation of light as to whether light has been detected at each of a plurality of pixels placed in the first line camera 16 and second line camera 18. Specifically, if light has been detected at each of the plurality of pixels, the signal levels of the captured image signals A and B are increased; if light has not been detected at each of the plurality of pixels, the signal levels of the captured image signals A and B are substantially 0.

In FIG. 5, the binarized signal D can be taken as an example of indicating a decision result as to whether the defective foreign matter 30 with the predetermined height or more is present on the surface of the wafer 26. Specifically, if the binarized signal D is at a high signal level, it indicates that the presence of defective foreign matter 30 with the predetermined height or more on the surface of the wafer 26 has been decided; if the binarized signal D is at a low signal level, it indicates that the non-existence of defective foreign matter 30 with the predetermined height or more on the surface of the wafer 26 has been decided.

With the surface defect inspection apparatus 10, even if a convex pattern has been formed at the illumination position P2, when the defective foreign matter 30 with the predetermined height or more is not present at the position P1 at the predetermined height, the binarized signal D is at a low signal level (see range (3) in FIG. 5).

That is, if a decision is made according to only the captured image signal A output from the first line camera 16 as to whether the defective foreign matter 30 is present, when the range is range (3) in FIG. 5, the captured image signal A falls into a low-to-medium signal level range, so the decision may become wrong. With the surface defect inspection apparatus 10, however, since the presence of defective foreign matter 30 is decided according to the captured image signal A output from the first line camera 16 and the captured image signal B output from the second line camera 18, this wrong decision is not made.

The binarized signal D obtained from the comparison between the differential signal C and the binarization reference signal E is input the image memory 46, as described above. While the first line camera 16 and second line camera 18 are undergoing main scanning, main scanning positional information is output from the camera main scanning control unit 40 to the image memory 46, according to the main scanning positions of the plurality of pixels placed in the first line camera 16 and second line camera 18.

The inspection and control unit 50 outputs a storage command to the image memory 46 in step S4 above. Accordingly, the binarized signal D, the move-to position information, and main scanning information are stored in relation in the image memory 46, the move-to position information being obtained when the captured image signals A and B, from which the binarized signal D is generated, are obtained.

Figure 6:
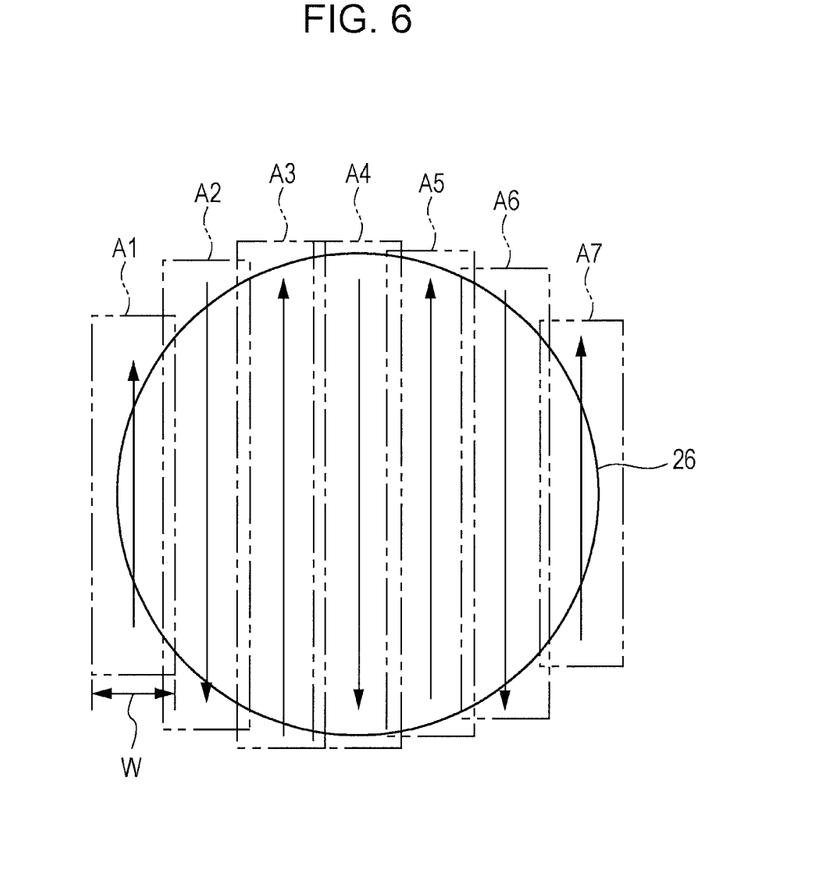
FIG. 6 illustrates movement traces of line laser beams directed to the wafer in FIG. 1.

Next, the inspection and control unit 50 decides in step S5 whether inspection for one laser beam width of the line laser beam 28 has been completed according to the move-to position information, which has been output from the moving stage control and driving circuit 42. Specifically, in this example, it is decided whether the first moving stage 22 has moved and the first sub-scanning range A1 illustrated in FIG. 6 has been thereby sub-scanned with the line laser beam 28. The symbol W in FIG. 6 indicates the width of the line laser beam 28.

The inspection and control unit 50 repeatedly executes steps S4 and S5 until it decides in step S5 that inspection for one laser beam width of the line laser beam 28 has been completed.

If the inspection and control unit 50 decides in step S5 that inspection for one laser beam width of the line laser beam 28 has been completed, the inspection and control unit 50 proceeds to step S6, where the inspection and control unit 50 decides whether inspection in all the inspection ranges set in step S1 has been completed. Specifically, in this example, it is decided whether the first sub-scanning range A1 to the seventh sub-scanning range A7 illustrated in FIG. 6 have been sub-scanned with the line laser beam 28.

If the inspection and control unit 50 decides in step S6 that inspection in all the inspection ranges has not been completed, the inspection and control unit 50 proceeds to step S7, where the inspection and control unit 50 outputs a sub-scanning range changing command to the moving stage control and driving circuit 42. The relevant actuator, not illustrated, is then actuated to move the second moving stage 24 in the X direction, setting the inspection range to a next sub-scanning range. Specifically, for example, if inspection in the first sub-scanning range A1 has been completed, the inspection range is set to the second sub-scanning range A2.

The inspection and control unit 50 repeatedly executes steps S4 to S7 until it decides in step S6 that inspection in all the inspection ranges has been completed.

Upon completion of inspection in all the inspection ranges set in step S1, the inspection and control unit 50 proceeds to step S8. In step S8, the inspection and control unit 50 first causes the defect deciding unit 48 to decide whether information stored in the image memory 46 is information about predetermined inspection ranges. In this decision, if the wafer 26 is circular but the first sub-scanning range A1 to the seventh sub-scanning range A7 are in strip form, information about an area in which the wafer 26 and the first sub-scanning range A1 to the seventh sub-scanning range A7 overlap is discriminated and extracted. Furthermore, the defect deciding unit 48 decides from the extracted information whether there is defective foreign matter (effective defect) having predetermined values, for which a two-dimensional size (size in the X and Y directions) has been predefined, or more.

If the defect deciding unit 48 decides that the defective foreign matter having the predetermined values is present, the defect deciding unit 48 outputs information about the defective foreign matter to the inspection and control unit 50. This information is extracted from the information, stored in the image memory 46, in which the binarized signal D, the move-to position information, and the main scanning information are related, the move-to position information being obtained when the captured image signals A and B, from which the binarized signal D is generated, are obtained.

Next, the inspection and control unit 50 proceeds to step S9, where the inspection and control unit 50 creates coordinate information 54 (defect map information) about the defective foreign matter 30 on the surface of the wafer 26 according to the information output from the defect deciding unit 48 in step S8. The coordinate information 54 about the defective foreign matter 30 includes the X and Y coordinates of the defective foreign matter 30, and the size of the defective foreign matter 30 in the X and Y directions. In this case, the inspection and control unit 50 is an example of the coordinate information output unit as a generator.

In step S10, the inspection and control unit 50 outputs the above coordinate information 54 to the operator console 52. Accordingly, the coordinate information 54 is displayed on the operator console 52 as the inspection result. In step S11, the inspection and control unit 50 further outputs the coordinate information 54 to the wafer inspection apparatus 60 described later.

If the inspection and control unit 50 decides in step S6 above that inspection in all the inspection ranges has been completed, the inspection and control unit 50 proceeds to step S12, where the inspection and control unit 50 outputs a move-to-inspection-termination-position command to the moving stage control and driving circuit 42. The actuators, not illustrated, are then actuated to move the first moving stage 22 and second moving stage 24, moving the wafer 26 to a predetermined inspection termination position.

If the inspection and control unit 50 decides in step S13 that the wafer 26 has moved to the inspection termination position, the inspection and control unit 50 terminates this series of processes. This completes the inspection carried out by the surface defect inspection apparatus 10.

Figure 7:
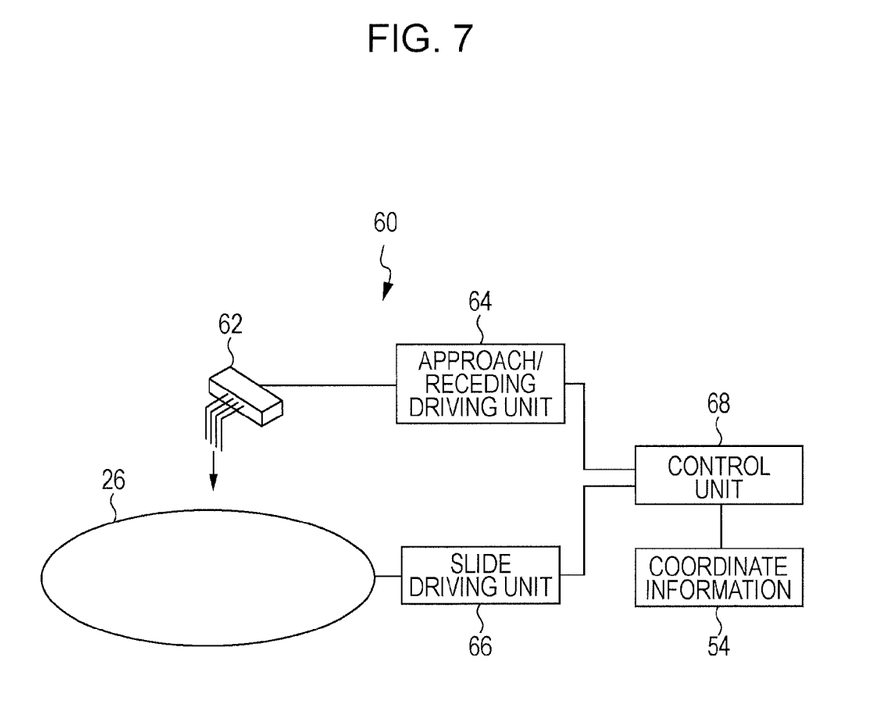
FIG. 7 illustrates the entire structure of a wafer inspection apparatus in an embodiment.

Next, the wafer 26, which the surface defect inspection apparatus 10 has inspected in this way, undergoes electric inspection on the wafer inspection apparatus 60 illustrated in FIG. 7.

The wafer inspection apparatus 60 includes a contact part 62, an approach/receding driving unit 64, a slid driving unit 66, and a control unit 68. The contact part 62 is a microelectromechanical systems (MEMS) probe card, for example. As for the contact part 62 in FIG. 6, only the main elements are depicted to facilitate understanding. The contact part 62 is moved up and down by a driving mechanism. The contact part 62 moves above the position P1 at the predetermined height, except its probes that come into contact with the wafer 26.

The approach/receding driving unit 64 causes the contact part 62 to approach and recede from the wafer 26, and the slid driving unit 66 causes a mounting table (not illustrated) on which the wafer 26 is placed to slide along the surface of the wafer 26. The control unit 68 controls the approach/receding driving unit 64 and slid driving unit 66.

To perform electric inspection on the wafer inspection apparatus 60, the contact part 62 is brought into contact with the IC of the wafer 26 with the wafer 26 placed on the mounting table. To change the position of the contact part 62 relative to the wafer 26, the mounting table is slid by the slid driving unit 66 with the contact part 62 separated from the wafer 26 by the approach/receding driving unit 64. In this electric inspection, the position of the contact part 62 is controlled so that contact part 62 avoids the defective foreign matter 30 according to the coordinate information 54 (defect map information) output from the surface defect inspection apparatus 10.

Electric inspection of the wafer 26 is carried out as described above. Upon completion of the electric inspection, this series of inspection for the wafer 26 is completed.

Next, effects and advantages in this embodiment will be described.

As described above, the surface defect inspection apparatus 10 in this embodiment decides from the captured image signal A output from the first line camera 16 and the captured image signal B output from the second line camera 18 whether the defective foreign matter 30 is present, making it possible to suppress the wrong decision. Specifically, even if minute irregularities have been formed at the illumination position P2 due to a convex pattern, it is possible to suppress the effect of the irregularities and decide whether the defective foreign matter 30 with the predetermined height or more is present on the wafer 26.

The captured image signal A output from the first line camera 16 and the captured image signal B output from the second line camera 18 undergo calculation in the operation circuit 34, and the differential signal C output from the operation circuit 34 is binarized in the binarization circuit 36. Accordingly, a decision result as to whether the defective foreign matter 30 with the predetermined height or more is present on the wafer 26 can be automatically obtained.

The coordinate information 54 about the defective foreign matter 30 on the surface of the wafer 26 is also automatically created from the binarized signal D, the move-to position information at a time when the captured image signals A and B, from which the binarized signal D is generated, are obtained, and the main scanning positional information. Since the wafer inspection apparatus 60 in this embodiment controls the position of the contact part 62 according to the coordinate information 54, a contact between the contact part 62 and the defective foreign matter 30 can be suppressed. As a result, damage of the contact part 62, which is generally regarded as being expensive, can be suppressed.

Next, variations of this embodiment will be described.

In this embodiment, the angle θ3 between the optical axis of the second line camera 18 and the surface of the wafer 26 may be set to a right angle. In this case, to suppress interference between the optical axis of the first line camera 16 and the optical axis of the second line camera 18, an optical system that bends an optical path may be added.

If, for example, the amount of reflected light from the defective foreign matter 30 can be secured, the angle θ2 between the optical axis of the first line camera 16 and the surface of the wafer 26 may be set to an acute angle.

A plurality of point light sources may be used instead of the line laser 14, and a plurality of photodetectors, each of which is equivalent to a pixel in the first line camera 16 and second line camera 18, may be used instead of the first line camera 16 and second line camera 18.

One point light source may be used instead of the line laser 14, and photodetectors may be used instead of the first line camera 16 and second line camera 18.

When photodetectors are used, the coordinate information 54 may be output according to information that includes the binarized signal output from the binarization circuit 36 and also includes information about a move-to position of the photodetector relative to the wafer 26.

One point light source may be used instead of the line laser 14, and light emitted from the point light source may be scanned by, for example, a rotational mirror, a galvanometer mirror, or the like.

A line light source that emits line light other than the line laser beam 28 may be used instead of the line laser 14.

With the wafer 26 fixed, the measurement system including the line laser 14, first line camera 16, and second line camera 18 may be moved, relative to the wafer 26, by a moving mechanism (not illustrated), which is an example of a relatively moving unit, or the like.

Although the surface defect inspection apparatus 10 has been applied to the wafer 26, the surface defect inspection apparatus 10 may be applied to any other target.

The signal waveforms of the captured image signals A and B illustrated in FIG. 4 and the information, illustrated in FIG. 5, about the signal levels of the captured image signals A and B may be displayed on the operator console 52. A worker may decide whether the defective foreign matter 30 is present according to the display provided on the operator console 52. Specifically, in FIGS. 4 and 5, if, for example, the signal level of the captured image signal A is substantially 0 or falls into the low-to-medium range and the signal level of the captured image signal B falls into the medium-to-high range, the worker may decide that the defective foreign matter 30 is not present. In FIGS. 4 and 5, if the signal level of the captured image signal A is high and the signal level of the captured image signal B is substantially 0, the worker may decide the defective foreign matter 30 is present.

Furthermore, the worker may obtain information about the coordinates of the defective foreign matter 30 on the surface of the wafer 26 according to the decision result as to whether the defective foreign matter 30 is present and to the move-to position information and main scanning positional information obtained when captured image signals on which the decision result is based were obtained. In this case, the signal waveform, illustrated in FIG. 4, of the binarized signal D and the information, illustrated in FIG. 5, about the signal level of the binarized signal D may be displayed on the operator console 52. The worker may obtain information about the coordinates of the defective foreign matter 30 on the surface of the wafer 26 according to the information, displayed on the operator console 52, about the binarized signal D and to the move-to position information and main scanning positional information described above.

Although an embodiment of the technology disclosed in this application has been described, the technology disclosed in this application is not limited to the above description; many variations are possible without departing from the intended scope of this application.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment of the present invention has been described in detail, it should be understood that the various changes, substitutions, and alterations could be made hereto without departing from the spirit and scope of the invention.

What is claimed is:

1. A surface defect inspection apparatus comprising:
   a light source that emits light to a first position on a surface of a target at an angle inclined with respect to the surface of the target;
   a first photodetector that detects first reflected light of the light from the light source, the first reflected light being reflected at the first position,
   a second photodetector that detects second reflected light of the light from the light source, the second reflected light being reflected at a second position on the surface of the target, the second position being different from the first position and closer to the light source than the first position and being separated vertically from the surface of the target by a given distance; and
   a determining unit that determines whether or not foreign matter is present on the surface of the target on a basis of detection results obtained from the first photodetector and the second photodetector, the determining unit determining that the foreign matter with a predetermined height or more is present on the surface of the target when the first reflected light is not detected by the first photodetector and the second reflected light is detected by the second photodetector.

2. A surface defect inspection apparatus comprising:
   a light source that emits light to a first position on a surface of a target at an angle inclined with respect to the surface of the target;
   a first photodetector that detects first reflected light of the light from the light source, the first reflected light being reflected at the first position;
   a second photodetector that detects second reflected light of the light from the light source, the second reflected light being reflected at a second position on the surface of the target, the second position being different from the first position and closer to the light source than the first position and being separated vertically from the surface of the target by a given distance; and
   a determining unit that determines whether or not foreign matter is present on the surface of the target on a basis of detection results obtained from the first photodetector and the second photodetector, the determining unit determining that the foreign matter with a predetermined height or more is not present on the surface of the target when the first reflected light is detected by the first photodetector and the second reflected light is not detected by the second photodetector and when first reflected light is detected by the first photodetector and the second reflected light is detected by the second photodetector.

3. The surface defect inspection apparatus according to claim 1, wherein
   the first photodetector outputs a first signal, a signal level of which is increased as an amount of the first reflected light detected by the first photodetector is increased,
   the second photodetector outputs a second signal, a signal level of which is increased as an amount of the second reflected light detected by the second photodetector is increased; and
   the determining unit includes:
   a first circuit that generates a differential signal between the first signal and the second signal,
   a second circuit that generates a binary signal obtained by binarizing the differential signal, and
   a third circuit that determines whether or not the foreign matter is present on the surface of the target on a basis of the binary signal.

4. The surface defect inspection apparatus according to claim 3, further comprising:
   a moving unit that moves the target relative to the light source, the first photodetector, and the second photodetector;
   an output unit that outputs relative position information on a position of the target relative to the first photodetector and the second photodetector; and
   a generator that generates coordinate information on a coordinate of the foreign matter on the surface of the target on a basis of the binary signal and the relative position information when the foreign matter is present on the surface of the target.

5. The surface defect inspection apparatus according to claim 3, wherein
   the light source is a line light source that emits line-like light to the first position on the surface of the target,
   each of the first photodetector and the second photodetector is a line camera including a plurality of detection areas allocated in a longitudinal direction of the light, and
   the apparatus further comprises:
   a moving unit that moves the target relative to the first photodetector and the second photodetector in a lateral direction of the light;
   an output unit that outputs relative position information on a position of the target relative to the first photodetector and the second photodetector; and
   a generator that generates coordinate information on a coordinate of the foreign matter on the surface of the target on a basis of the binary signal and the relative position information when the foreign matter is present on the surface of the target.

6. A surface defect inspection method comprising:
   emitting light from a light source to a first position on a surface of a target at an angle inclined with respect to the surface of the target; and
   determining whether or not foreign matter is present on the surface of the target on a basis of detection results obtained from a first photodetector and a second photodetector, the first photodetector detecting first reflected light of the light from the light source, the first reflected light being reflected at the first position, the second photodetector detecting second reflected light of the light from the light source, the second reflected light being reflected at a second position on the surface of the target, the second position being different from the first position and closer to the light source than the first position and being separated vertically from the surface of the target by a given distance,
   wherein the determining determines that the foreign matter with a predetermined height or more is present on the surface of the target when the first reflected light is not detected by the first photodetector and the second reflected light is detected by the second photodetector.

7. The surface defect inspection method according to claim 6, further comprising:
   moving the target relative to the light source, the first photodetector, and the second photodetector;

outputting relative position information on position of the target relative to the first photodetector and the second photodetector; and generating coordinate information on a coordinate of the foreign matter on the surface of the target on a basis of the relative position information and determination results obtained from the determining.

8. The surface defect inspection method according to claim 6, wherein the light source is a line light source that emits line-like light to the first position on the surface of the target;

each of the first photodetector and the second photodetector is a line camera including a plurality of detection areas allocated in a longitudinal direction of the light; and the determining includes moving the target relative to the first photodetector and the second photodetector in a lateral direction of the light, outputting relative position information on position of the target relative to the first photodetector and the second photodetector, and generating coordinate information on a coordinate of the foreign matter on the surface of the target on a basis of the relative position information and determination results obtained from the plurality of detection areas.

9. The surface defect inspection method according to claim 6, wherein the target is a wafer.

10. A surface defect inspection method comprising:

emitting light from a light source to a first position on a surface of a target at an angle inclined with respect to the surface of the target; and determining whether or not foreign matter is present on the surface of the target on a basis of detection results obtained from a first photodetector and a second photodetector, the first photodetector detecting first reflected light of the light from the light source, the first reflected light being reflected at the first position, the second photodetector detecting second reflected light of the light from the light source, the second reflected light being reflected at a second position on the surface of the target, the second position being different from the first position and closer to the light source than the first position and being separated vertically from the surface of the target by a given distance wherein the determining determines that the foreign matter with a predetermined height or more is not present on the surface of the target when the first reflected light is detected by the first photodetector and the second reflected light is not detected by the second photodetector and when the first reflected light is detected by the first photodetector and the second reflected light is detected by the second photodetector.

* * * * *

UNITED STATES PATENT AND TRADEMARK OFFICE
CERTIFICATE OF CORRECTION

| | | |
|---|---|---|
| PATENT NO. | : 8,854,613 B2 | Page 1 of 1 |
| APPLICATION NO. | : 13/352663 | |
| DATED | : October 7, 2014 | |
| INVENTOR(S) | : Katsumi Fujihara | |

It is certified that error appears in the above-identified patent and that said Letters Patent is hereby corrected as shown below:

In the Claims

Column 11, Line 15, in Claim 1, delete "position," and insert -- position; --, therefor.

Signed and Sealed this
Twenty-fourth Day of February, 2015

Michelle K. Lee
*Deputy Director of the United States Patent and Trademark Office*